US 6,544,208 B2

(12) United States Patent
Ethier et al.

(10) Patent No.: US 6,544,208 B2
(45) Date of Patent: Apr. 8, 2003

(54) IMPLANTABLE SHUNT DEVICE

(76) Inventors: C. Ross Ethier, 203 Haddington Ave., Toronto, Ontario (CA), M5M 2P7; Arthur J. Sit, 23 McGill St., Toronto, Ontario (CA), M5B 1H3; Molly S. Shoichet, 15 Austin Crescent, Toronto, Ontario (CA), M5R 3E4

( * ) Notice: Subject to any disclaimer, the term of this patent is extended or adjusted under 35 U.S.C. 154(b) by 42 days.

(21) Appl. No.: 09/750,024

(22) Filed: Dec. 29, 2000

(65) Prior Publication Data

US 2002/0087111 A1 Jul. 4, 2002

(51) Int. Cl.[7] .............. A61M 5/00; A61M 1/00; A61F 9/00; A61F 11/00; A61B 3/16
(52) U.S. Cl. .................. 604/8; 604/9; 604/10; 604/27; 604/28; 604/30; 606/107; 606/108; 600/398; 128/898; 251/5; 137/844
(58) Field of Search .............. 600/398; 606/107, 606/108; 604/8–10, 27–28, 30; 128/898; 251/5; 137/844

(56) References Cited

U.S. PATENT DOCUMENTS

| 3,441,245 A | * | 4/1969 | Holland et al. ............... 251/5 |
| 3,759,289 A | * | 9/1973 | De Wall ..................... 137/525 |
| 3,886,948 A | | 6/1975 | Hakim |
| 3,924,635 A | | 12/1975 | Hakim |
| 4,457,757 A | | 7/1984 | Molteno |
| 4,552,552 A | | 11/1985 | Polaschegg et al. |
| 4,886,488 A | | 12/1989 | White |
| 5,071,408 A | | 12/1991 | Ahmed |
| 5,071,411 A | | 12/1991 | Hillstead |
| 5,171,213 A | | 12/1992 | Price, Jr. |
| 5,192,265 A | | 3/1993 | Drake et al. |
| 5,338,291 A | | 8/1994 | Speckman et al. |
| 5,346,464 A | | 9/1994 | Camras |
| 5,411,473 A | | 5/1995 | Ahmed |
| 5,454,796 A | | 10/1995 | Krupin |
| 5,626,558 A | | 5/1997 | Suson |
| 5,743,868 A | | 4/1998 | Brown et al. |
| 6,007,511 A | | 12/1999 | Prywes |
| 6,050,970 A | | 4/2000 | Baerveldt |
| 6,138,984 A | * | 10/2000 | Abell ........................... 251/5 |

* cited by examiner

*Primary Examiner*—Gregory Huson
*Assistant Examiner*—Anuradha Ramana
(74) *Attorney, Agent, or Firm*—Nancy E. Hill; Hill & Schumacher

(57) ABSTRACT

A bioinert implantable shunt device useful for controlling internal pressure includes a valve apparatus, a device for attaching the valve apparatus and an inlet tube. The valve apparatus includes an inlet port, an outlet port, a flexible tube connected therebetween and a pressurized enclosure. The flexible tube is positioned inside the pressurized enclosure whereby fluid flow from the inlet port to the outlet port is dependent on a differential pressure between a pressure in the flexible tube and a pressure outside the flexible tube in the pressurized enclosure. The inlet tube is connected to the inlet port of the valve apparatus. The pressurized enclosure may include a housing and a semi-permeable membrane in a wall of the housing whereby fluid can pass through the semi-permeable membrane into the pressurized enclosure thereby increasing the pressure in the pressurized enclosure. The implantable shunt device may be for use in the treatment of glaucoma. Further, there is provided a method of reducing intraocular pressure including the, steps of attaching a biocompatible implantable shunt device to the scleral surface of an eye and inserting an inlet tube into the anterior chamber of the eye.

25 Claims, 7 Drawing Sheets

IMPLANTABLE SHUNT DEVICE

FIELD OF THE INVENTION

This invention relates to surgical implants and in particular surgically implantable shunt devices for draining aqueous humor from an eye.

BACKGROUND OF THE INVENTION

Glaucoma is a group of ocular diseases that are major causes of blindness. Most types of glaucoma are characterized by elevated pressure within the eye, the so-called intraocular pressure (IOP). Current theories suggest that this elevated IOP causes damage to the optic nerve in susceptible patients, resulting in vision impairment. Existing therapies for glaucoma attempt to decrease IOP and thus reduce optic nerve damage.

There are several approaches to reducing IOP. One type of surgical approach is to provide an alternate drainage pathway for fluid from the eye, thereby reducing IOP. Specifically, the approach is to implant an artificial shunt in the eye. The function of this shunt is to drain ocular fluid (aqueous humor) from the anterior chamber of the eye to the sub-conjunctival space overlying the eye. Such shunts are subject to two important limitations:

1) In the short term (hours to days) after surgical implantation of the shunt device, IOP can drop to very low values due to the shunt providing an essentially unrestricted egress route for aqueous humor from the eye. Until scar tissue forms at the outflow end of the shunt, this low IOP can cause sight-threatening complications and must therefore be avoided. Some existing shunts attempt to overcome this problem by inserting fluid resistors in the shunt. However, this may result in an excessively high final IOP requiring further pressure-lowering therapies.

2) Currently, there is no mechanism for selecting a long-term (months to years) level of post-operative IOP. Essentially, long-term post-operative IOP is a function of scar tissue formation and other uncontrollable variables, If IOP is not sufficiently lowered by shunt implantation, additional pressure lowering treatments are needed. No device has previously attempted to allow selection of specific target IOPs.

The use of aqueous shunts is well-established in the treatment of glaucoma, with the earliest documented procedure occurring in 1906 [Shocket, 1986]. Modern shunts are based on the design introduced by Molteno [1969; U.S. Pat. No. 4,457,757]. Essentially, Molteno's implant consisted of a 1 mm acrylic tube attached to a round episcieral acrylic plate. The tube passed from the anterior chamber through the limbus of the eye to the plate, which was placed subconjunctivally and sutured to the sclera. As fluid drained from the anterior chamber, through the tube, and emptied onto one side of the episcleral plate, the space between the plate and the conjunctiva was maintained, forming a "bleb". Unlike conventional glaucoma filtration surgery, the size of the bleb was controlled by the size of the episcleral plate. By making the plate sufficiently large [Molteno et al., 1977; Heuer et al., 1992; Smith et al., 1993], the bleb filtering surface could be made sufficiently large to maintain a satisfactorily low IOP.

The most significant barrier to success of an aqueous drainage implant appears to be short-term post-operative complications [Hitchings et al., 1987; Krupin et al., 1976; White, 1992]. In particular, post-operative hypotony (subnormal IOP) is a significant problem [Hitchings et al., 1987; White, 1992]. To address this problem, shunts have been developed that incorporate valves [Krupin et al., 1976; Krupin et al., 1988; White, 1992; Prata et al., 1995]. In principle, these valves are intended to be pressure control valves that establish a minimum IOP. However, Prata et al. [1995] tested several valve designs (Ahmed Implant, New World Medical Inc.; Krupin Eye Disk, Hood Laboratories; OptiMed Implant, OptiMed Inc.) and found that these implants were not true valves but simply flow limitation devices with no detectable opening or closing pressure. While these implants may therefore be an improvement over non-valved implants, they still do not address the essential problem of accurately controlling post-operative IOP.

The implant that is currently believed to provide some valve action is that of Ahmed (U.S. Pat. Nos. 5,071,408 and 5,411,473). The former patent states; "Disclosed is a medical valve comprising a pair of plates holding in tension a membrane folded over to form a chamber with an elongated, slit-like opening along adjoining edges. The plates include interlocking members which interlock the plates together. An inlet tube in communication with the chamber extends outwardly from the plates." The membrane under tension disclosed in this patent is designed to act as a valve, in which the leaflets of the membrane are forced apart when the pressure in the eye exceeds some set pressure. However, as mentioned above, this device does not provide a true opening pressure. Also, its effective pressure range is critically dependent on the tension in the membrane, and therefore is sensitive to manufacturing issues.

Accordingly it would be advantageous to provide a shunt device that improves the accuracy and reliability of controlling and regulating the pressure within the eye when aqueous humor fluid drains from the eye through the shunt device. Further it would be advantageous to provide a similar device for use in other medical applications where drainage of fluid is required.

SUMMARY OF THE INVENTION

One aspect of the present invention is a bioinert implantable shunt device useful for controlling internal pressure. It includes a valve apparatus, a means for attaching the valve apparatus and an inlet tube. The valve apparatus includes an inlet port an outlet port, a flexible tube connected therebetween and a pressurized enclosure. The flexible tube is positioned inside the pressurized enclosure whereby fluid flow from the Inlet port to the outlet port is dependent on a differential pressure between a pressure in the flexible tube and a pressure outside the flexible tube in the pressurized enclosure. The inlet tube is connected to the inlet port of the valve apparatus. The pressurized enclosure may include a housing and a semi-permeable membrane in a wall of the housing whereby fluid can pass through the semi-permeable membrane into the pressurized enclosure thereby increasing the pressure in the pressurized enclosure. The implantable shunt device may be for use in the treatment of glaucoma.

In another aspect of the invention there is provided a method of reducing intraocular pressure including the steps of attaching a bioinert implantable shunt device to the scleral surface of an eye and inserting an inlet tube into the anterior chamber of the eye. The implantable shunt device includes a valve apparatus having an inlet port, an outlet port, a flexible tube connected therebetween and a pressurized enclosure. The flexible tube is positioned inside the pressurized enclosure whereby fluid flow from the inlet port to the outlet port is dependent on a differential pressure between a pressure in the flexible tube and a pressure outside the flexible tube in the pressurized enclosure. The inlet tube is connected to the inlet port of the valve apparatus.

Further features of the invention will be described or will become apparent in the course of the following detailed description.

BRIEF DESCRIPTION OF THE DRAWINGS

The invention will now be described by way of example only, with reference to the accompanying drawings, in which.

DETAILED DESCRIPTION OF THE INVENTION

Figure 1:
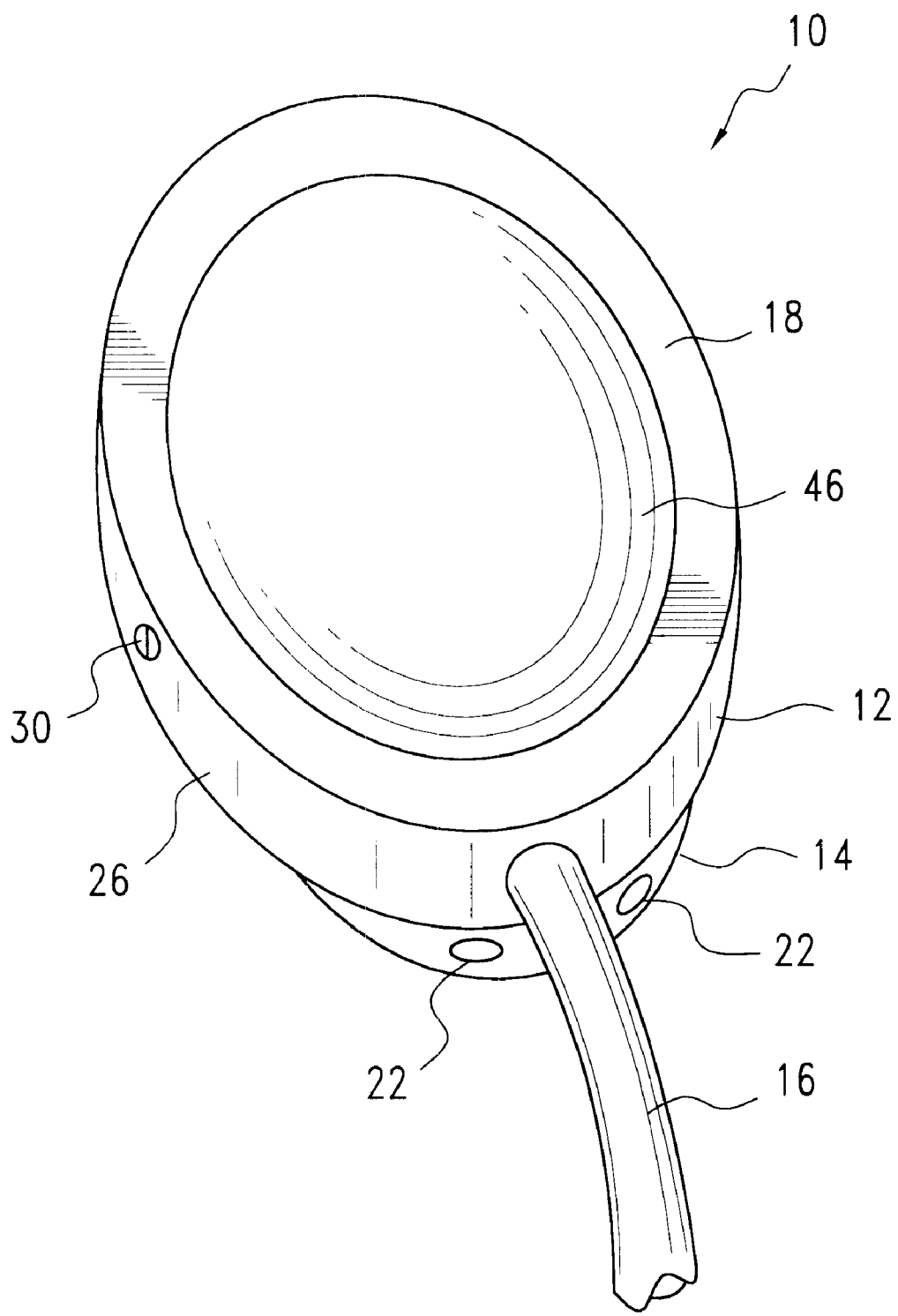
FIG. 1 is a top view of an implantable shunt device of the present invention.

FIG. 1 illustrates the implantable shunt device generally at 10. The implantable shunt device includes a valve assembly 12, a suture plate 14 and an inlet tube 16.

Figure 7:
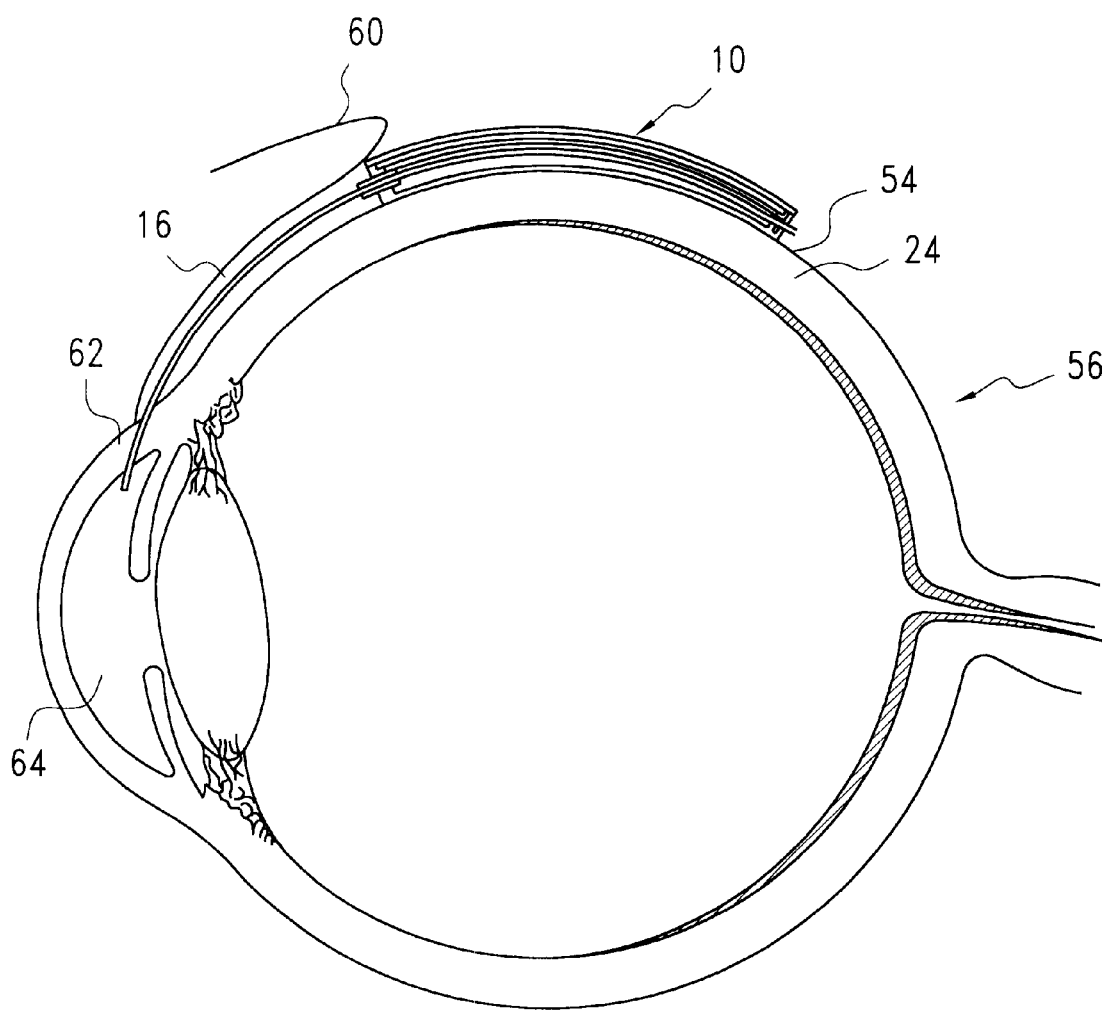
FIG. 7 is a cross sectional view of an eye showing the implantable shunt device of the present invention attached thereto.

Preferably the inlet tube 16 is to be made of some type of flexible plastic or rubber material that is well tolerated by the body. One such suitable material is Silastic™, manufactured by Dow-Corning Company. The diameter of the tube shall be such as to allow easy implantation of the end of the tube through the limbus and hence into the eye while not being so small as to be easily occluded by cells or other particulate materials. A suitable internal diameter for this tube is approximately 0.3 to 0.8 mm, The length of the tube is adapted to easily reach the anterior chamber of the eye while the main body of the shunt is located on the surface of the eye in the space between the superior rectus and lateral rectus, or the space between the superior rectus and the medial rectus near the insertion points of the superior rectus muscle, or at any other location on the eye that is convenient for the surgeon (as shown in FIG. 7). Because of anatomical variations and differences in surgical technique, this can be best accomplished by making the inlet tube 4 cm or longer, and having it cut by the surgeon during implantation.

Details of the valve assembly can best be seen in FIG. 1 through FIG. 4. Preferably a valve housing 18 is constructed of polymethyl methacrylate or other bioinert semi-rigid plastic. The term bioinert is used herein to include biocompatible and biostable materials. Preferably the overall housing dimensions are approximately elliptical with a major axis of 15 mm and a minor axis of 10 mm, with an overall thickness of 2–3 mm. In addition, the base or lower surface 20 of the housing 18 is rounded allowing it to be shaped like a portion of the surface of a sphere having a radius of curvature of approximately 12 mm. This rounding allows the housing to lie comfortably on the surface of the eye and facilitates its attachment to the eye.

Attached to the valve housing 18 is a suture plate 14 with suture passage holes 22 that allow the device to be conveniently sutured to the sclera 24 (as shown in FIG. 7). Passing through the valve housing wall 26 are a filling port 28, sealed with a filling port screw 30 and a purge port 32, sealed with a purge port screw 34 (best seen in FIG. 4). These ports are used in the assembly of the device and then typically remain sealed for the duration of use.

Figure 2:
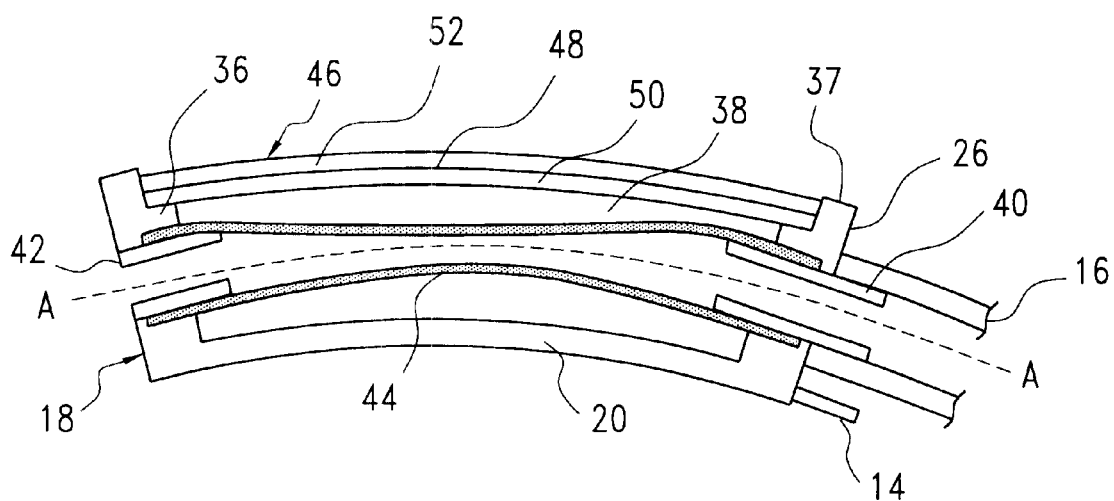
FIG. 2 a cross sectional view of the implantable shunt device.

FIG. 2 depicts a cross-sectional view of a preferred embodiment of the shunt device. Preferably the valve housing 18 is manufactured so that the interior of the housing is open, leaving only a "base" and "walls". The thickness of this base 20 is approximately 0.3 mm. The walls 26 are shaped so as to incorporate a shoulder 36 (FIG. 2) approximately 0.3 mm below the top 37 of the valve housing 18. Above this shoulder the walls are approximately 0.3 mm thick; below the shoulder they are approximately 0.8 mm thick. The portion of the valve housing below the shoulder will be referred to as the "osmotic pressure chamber" 38. The housing is fitted with two holes, one at either end at the level of the osmotic pressure chamber. These holes are sized so as to accept an inlet nipple 40 and an outlet nipple 42, and form the inflow port and the outflow port to which the collapsible flexible tube 44 attaches. A suitable diameter for these holes is 0.8 mm.

FIG. 2 also depicts details of the membrane assembly 46 which is a sandwich consisting of a filtration or semi-permeable membrane 48 inserted and affixed firmly between an upper 50 and lower 52 support grating. The semi-permeable membrane 48 is selected with a pore size that allows passage of electrolytes and small molecules, but rejects larger molecular weight solutes. In particular, the membrane pores shall be sized so as to completely, or nearly completely, reject a solute that is dissolved in the fluid contained in the osmotic pressure chamber. Preferably the support gratings 50, 52 are constructed of porous sintered plastic, such as polymethyl methacrylate or other bioinert plastic. Support gratings 50, 52 reduce deformation of the semi-permeable membrane 48 while allowing unimpeded passage of fluid and solutes. Significant deformation of the semi-permeable membrane will make it difficult to predict the osmotic pressure generated by the fluid and solutes, accordingly as described above it is advantageous to reduce deformation of the semi-permeable membrane 48. The pore size for these plastic gratings 50, 52 is chosen to minimize the risk of occlusion of the membrane while allowing free passage through the grating of fluid and solutes. The support gratings 50, 52 will be sized so as to snugly and tightly fit into the valve housing so that the lower surface of the lower support grating rests on the shoulder 36 of the housing 18 and the upper surface of the upper support grating 52 is flush with the upper edge of the walls of the valve housing. A suitable thickness for the gratings is 0.15 mm for each grating. The membrane 48 will be sized so that it is slightly larger than the support gratings, such that when the membrane module "sandwich" is put together, there is approximately 0.5 mm of membrane protruding beyond the edges of the support gratings. This protruding membrane will be used to help seal the membrane assembly 46 into the valve housing 18.

Alternatively, the membrane support gratings 50 and 52 are solid plastic plates having multiple holes of approximately 0.2 mm diameter, encompassing approximately 50% of the grating surface.

Figure 3:
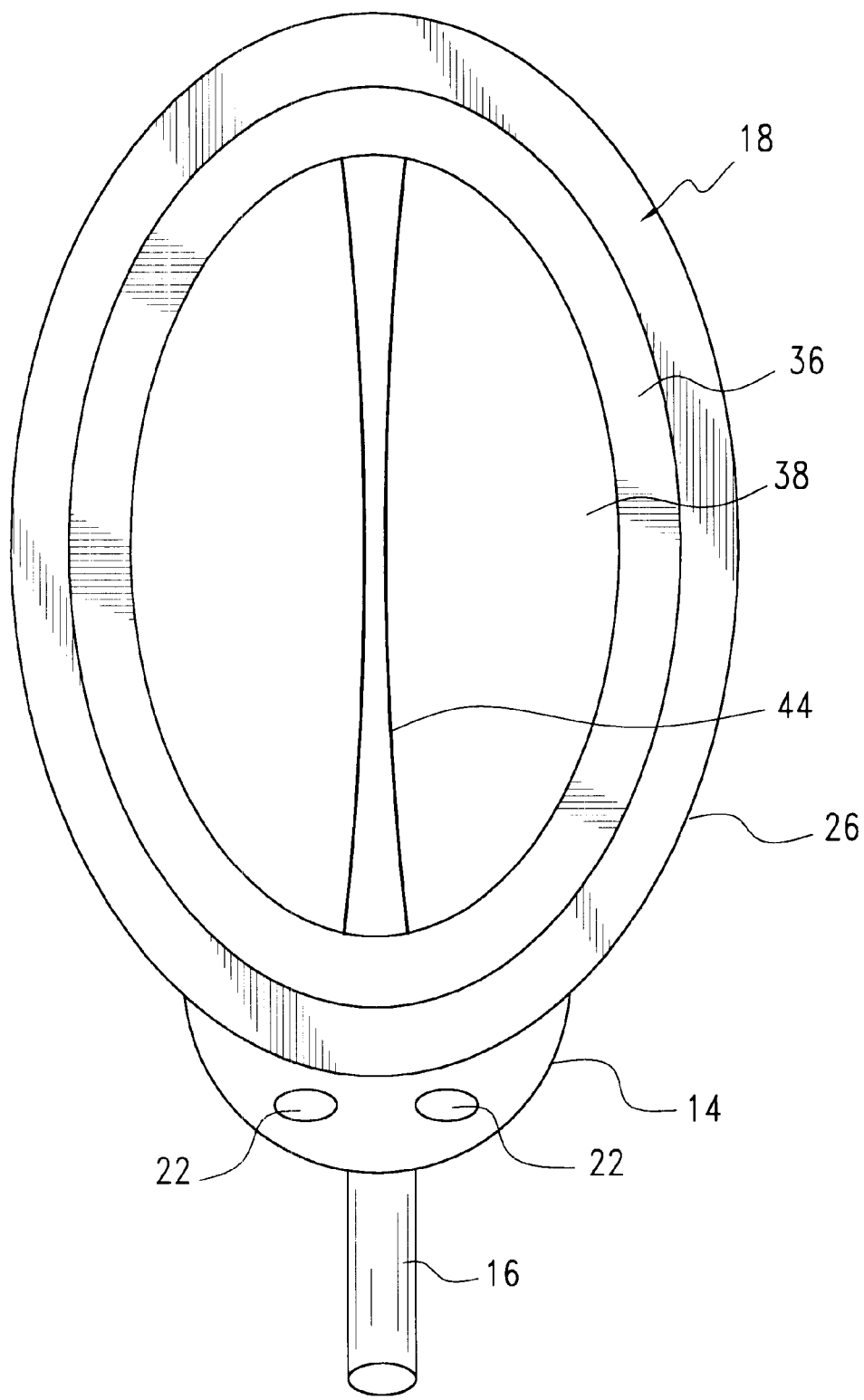
FIG. 3 a top view of the implantable shunt device with the semi-permeable membrane module removed.

FIG. 3 depicts a plan view from above the device with the membrane module removed. The collapsible flexible tube 44 is seen as it would appear in an assembled device prior to attachment of the membrane module. It consists of a thin, highly flexible tube that can be completely collapsed under external pressure. Collapsible flexible tube may be a very thin-walled Silastic™ tube, but other flexible, bioinert tubing may be used as well. To allow complete collapse of the tube, the preferred embodiment incorporates a tube having a flat cross section.

Figure 4:
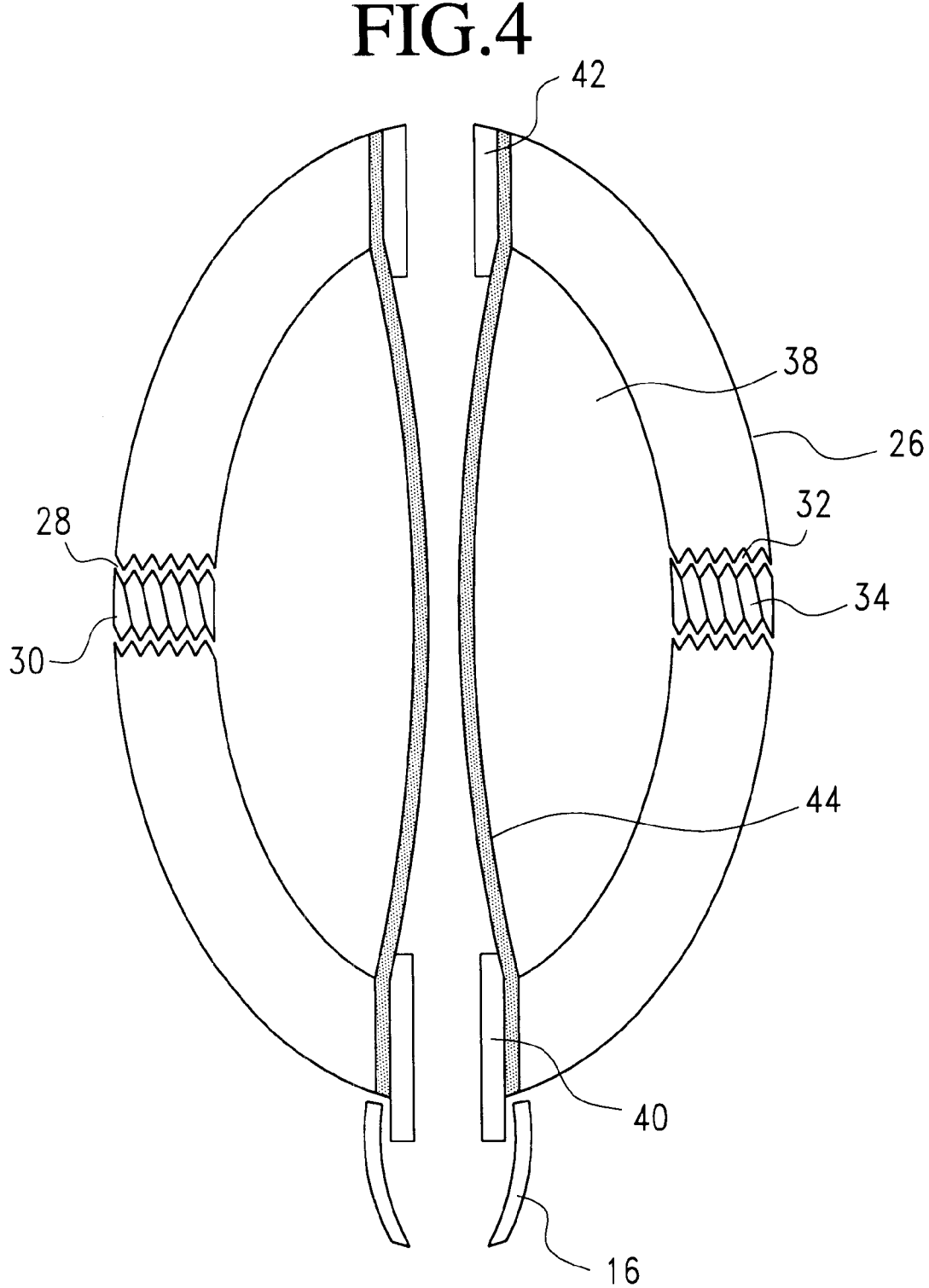
FIG. 4 a horizontal cross sectional view of the device at the level of the flexible tube along section A—A of FIG. 2.

FIG. 4 depicts a cross-sectional view through the assembled device at the mid-level of the inlet and outlet nipples 40, 42. This mid-level corresponds to Section A—A shown in FIG. 2. The ends of the collapsible tubing 44 are attached to the inlet 40 and outlet 42 nipples, which insert snugly into the inflow and outflow ports of the valve housing 18. When assembled, the end of the outlet nipple 42 should be approximately flush with the outer surface of the wall of the valve module that incorporates the outflow port. The inlet nipple 40 has a longer extension that protrudes beyond the outer surface of the wall 26 of the valve housing 18. The inlet tube 16 is attached to this extension when the device is assembled. The filling port screw 30 is used to fill the osmotic pressure chamber with fluid at the end of the assembly process. The purge port screw 34 is used to simultaneously expel any air within the osmotic pressure chamber.

During assembly the collapsible flexible tube 44 is attached to the valve housing 18 using a suitable adhesive so as to prevent fluid leaks. The membrane assembly 46 is then inserted into the valve housing 18. This is sealed by a bead of adhesive placed around the upper walls 26 of the valve housing 18 (above the level of the shoulder 36). During this procedure the support gratings 50, 52 and the protruding membrane 48 are sealed to the walls of the valve housing 18.

After attaching the membrane assembly 46, the osmotic pressure chamber 38 is filled with a solution that generates an osmotic pressure. The composition of this solution is chosen to satisfy the following constraints. First, preferably the solution is water-based, so that suitable osmotic pressures are generated when the solution is in communication with bodily fluids across the semi-permeable membrane 48. Second, preferably the solute(s) in the solution is a high molecular weight material that is effectively unable to cross the filtration membrane 48. Third, preferably the solute(s) is resistant to hydrolysis or other breakdown mechanisms at body temperature. Fourth, these solutes are bioinert, so that if the membrane breaks or mechanical integrity of the valve is otherwise breached, leakage of these solutes into the surrounding tissue does not pose a health risk. Fifth, preferably the solute(s) is capable of generating osmotic pressures in the ranges of 0 to 40 mmHg. A suitable solute is high molecular weight dextran, for example that sold by Sigma Chemical Company with a molecular weight of between 50 and 2,000,000 Da. One of the advantages of this design is that the osmotic pressure obtained when the device is placed in vivo (and hence the valve opening/closing pressure) can be easily altered by changing the concentration of the solute in the osmotic pressure chamber.

The osmotic chamber is filled with solution through the filling port 28, with the purge port 32 open to allow air to exit the osmotic pressure chamber 38.

The completely assembled device 10 is sutured to the scleral surface 54 of the eye 56 in the space between the superior rectus and lateral rectus and is covered with the conjunctiva 60. Alternatively the device 10 is sutured between the superior rectus and the medial rectus. Alternatively the device 10 is glued into place using a fibrin glue or collagen-based glue. The inlet tube 16 is inserted through the limbus 62 into the anterior chamber 64 after being cut to the proper length based on the anatomy of the individual eye.

Fluid flows from the anterior chamber 64 through the device 10 in the following order: through the inlet tube 16, the inlet nipple 40, the collapsible flexible tube 44, the outlet nipple 42, and then exits the device 10. The fluid pools around the device, below the conjunctiva, forming a bleb. Fluid ultimately filters through the bleb into the lymphatics of the orbit. Fluid from the bleb also filters through the semi-permeable ultrafiltration membrane 48 into the osmotic pressure chamber 38 surrounding the collapsible flexible tube 44. This allows a valve opening pressure to be established that will govern the intraocular pressure postoperatively.

Figure 5:
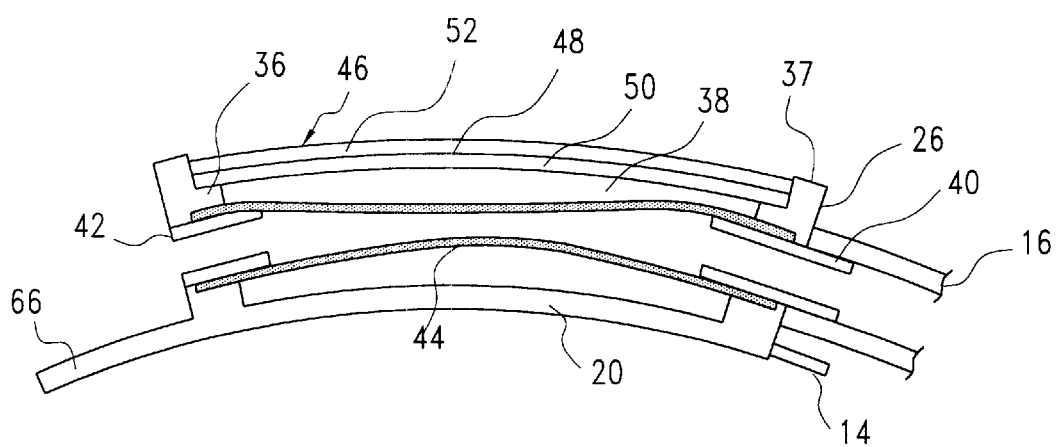
FIG. 5 is a cross sectional view through the device showing an alternate embodiment comprising a larger base plate.

There are a number of alternate embodiments that involve changes in how the fluid exits the device. One such embodiment is shown in FIG. 5 wherein the surface area of the valve housing base 20 is extended by a valve housing base extension 66 that protrudes beyond the surface where the outlet nipple 42 terminates. This will have the effect of increasing the plan area of the device and thus promoting the formation of a larger fluid filtration bleb. The presence of a very large filtering bleb is useful in situations for which a very low IOP is desired.

Figure 6:
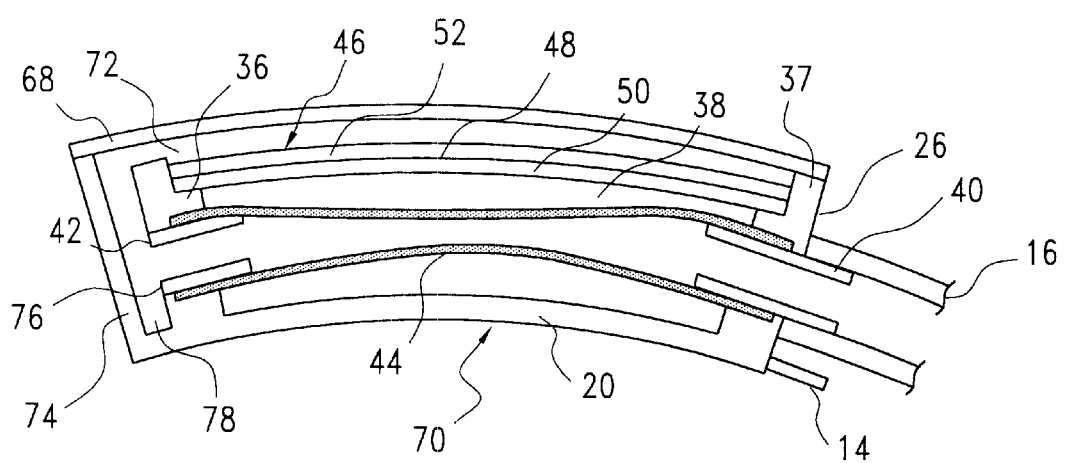
FIG. 6 is a cross sectional view through the device showing a second alternate embodiment comprising a porous cover and associated fluid drainage channels.

A second alternate embodiment shown in FIG. 6 involves addition of a porous cover 68 to the upper surface of the valve assembly 70 This porous cover 68 is spaced from the upper membrane support grating 52 by a small gap which defines an outer chamber 72 which has a depth of 0.2 to 0.5 mm. As well, the shape of the valve housing wall 74 is changed at the distal end 76 so as to provide a small drainage reservoir 78 into which the fluid can drain after it exits the outlet nipple 42. This drainage reservoir 78 is in direct communication with the outer chamber 72 between the upper membrane support grating 52 and the porous cover 68. Fluid leaving the exit nipple 42 therefore fills the drainage reservoir 78, then passes into the outer chamber 72, before finally exiting the device through the porous upper cover 68 or filtering through the membrane assembly 46 to pass into the osmotic pressure chamber 38. This embodiment has a number of advantages. First, by suitable choice of pore size in the porous cover 68, the porous cover can act to protect the upper membrane support grating 52 from cellular adhesion or other events. Second, this embodiment ensures that there will always be fluid bathing the outer surface of the upper membrane support plate 52. Third, the fluid that leaves this embodiment of the device seeps out through a multitude of holes in the porous cover 68. This renders the device much less susceptible to blockage by scar tissue associated with the filtering bleb.

The implantable shunt device 10 of the present invention is a valved glaucoma drainage implant that allows true and precise regulation of pressure. One novel feature of the device is the use of a fluid-filled collapsible tube attached at both ends to rigid tubes, one of which allows the inflow of aqueous humor or other fluid, and the second of which allows the outflow. The collapsible portion of the tube is housed in a pressurized rigid enclosure. When pressure inside the collapsible tube exceeds a critical value, the tube opens and allows free fluid passage; otherwise, the tube is collapsed and prevents fluid passage. In this way the device acts as a one-way valve having an opening pressure controlled by the elastic properties of the collapsible tube and the pressure in the rigid enclosure. The second novel feature of our device is the use of osmotic effects to generate the pressure inside the rigid enclosure. A semi-permeable membrane supported by porous plates is incorporated into an opening in the rigid housing. The outer surface of this membrane is in communication with bodily fluids, e.g. fluids in the subconjuctival space, while the inner surface is in communication with the interior of the rigid enclosure. The rigid enclosure is filled with a solution containing a solute that generates an osmotic pressure when the outer membrane surface is in communication with bodily fluids. Adjusting the composition of the solution in the rigid enclosure can accurately control the amount of osmotic pressure generated. Because the osmotic pressure indirectly controls the opening pressure of the valve, this has the advantage of allowing precise regulation of the valve opening pressure. It is relatively easy to accurately control the osmotic pressure of a solution, and thus this device is easy to manufacture with high quality control. In theory, the desired opening pressure could even be set peri-operatively by filling the rigid enclosure with a suitable fluid just prior to implantation. This design also has the advantage of being unaffected by changes in local ambient pressure, e.g. variations in atmospheric pressure.

It will be appreciated by those skilled in the art that the device of the present invention can also be used in situations in which a defined pressure is required in a chamber from which fluid is draining at low flow rate. One such related problem is that of hydrocephalus or any other condition associated with raised intracranial pressure, such as benign intracranial hypertension. Hydrocephalus is a condition in which there is excess intracranial pressure leading to dilatation of the brain ventricles with excess cerebrospinal fluid. Treatment of these conditions involves implantation of a shunt designed to drain cerebrospinal fluid from a cerebral ventricle to some other location in the body, frequently the peritoneal cavity. In such situations it is desirable to maintain a fixed intracranial pressure, and the device that we describe could be used for this purpose. The valve assembly of the present invention would be placed at some suitable location in the cerebrospinal fluid drainage tube and would provide control of pressure by a mechanism the same as that described for the drainage of ocular fluid.

It will be appreciated that the above description related to the invention by way of example only. Many variations on the invention will be obvious to those skilled in the art and such obvious variations are within the scope of the invention as described herein whether or not expressly described.

What is claimed as the invention is:

1. A bioinert implantable shunt device useful for controlling internal pressure and comprising:

a valve apparatus having an inlet port, an outlet port, a flexible tube connected therebetween and a pressurized enclosure, the flexible tube being positioned inside the pressurized enclosure whereby fluid flow from the inlet port to the outlet port is dependent on a differential pressure between a pressure in the flexible tube and a pressure outside the flexible tube in the pressurized enclosure and the pressurized enclosure having a housing, a semi-permeable membrane in a wall of the housing and a liquid solution in the pressurized enclosure whereby fluid can pass through the semi-permeable membrane into the pressurized enclosure thereby increasing the pressure of the liquid solution in the pressurized enclosure;

a means for attaching the valve apparatus; and an inlet tube connected to the inlet port of the valve apparatus.

2. An implantable shunt device as claimed in claim 1 wherein the semi-permeable membrane is sandwiched between an upper support grating and a lower support grating.

3. An implantable shunt device as claimed in claim 2 wherein the pressurized enclosure has a filling port, a filling port stopper, a purge port and a purge port stopper whereby during filing of the pressurized enclosure the liquid solution is injected into the pressurized enclosure through the filling port and any gases that are in the pressurized enclosure is purged through the purge port.

4. An implantable shunt device as claimed in claim 3 wherein the housing of the pressurized enclosure has a bottom wall, a top wall and a side wall and wherein the semi-permeable membrane is positioned in the top wall, the inlet port is positioned in the side wall and the outlet port is positioned in the side wall.

5. An implantable shunt device as claimed in claim 4 further including a porous cover spaced from the semi-permeable membrane defining an outer chamber therebetween and further including a drainage reservoir adjacent to the outlet port and in flow communication with the outer chamber.

6. An implantable shunt device as claimed in claim 4 wherein the inlet tube is a flexible plastic tube.

7. An implantable shunt device as claimed in claim 4 wherein the inlet tube is a flexible rubber tube.

8. An implantable shunt device as claimed in claim 4 wherein the housing is made from a semi-rigid plastic.

9. An implantable shunt device as claimed in claim 4 wherein the housing is made from polymethyl methacrylate.

10. An implantable shunt device as claimed in claim 4 wherein the flexible tube is a thin-walled Silastic™ tube.

11. An implantable shunt device as claimed in claim 4 wherein the housing is generally elliptical having a major axis and a minor axis and the inlet port is positioned at one end of the major axis and the outlet port is positioned at the other end of the major axis.

12. An implantable shunt device as claimed in claim 11 wherein the attachment means is a suture plate having suture holes formed therein and the suture plate is attached to the valve assembly.

13. An implantable shunt device as claimed in claim 12 wherein the bottom wall is round and has a bottom surface shaped like a portion of a surface of a sphere.

14. An implantable shunt device as claimed in claim 13 further including a valve housing base extension that extends outwardly from the base of the housing and protrudes outwardly from the bottom wall proximate to the outlet port.

15. An implantable shunt device as claimed in claim 1 wherein the liquid solution is water based.

16. An implantable shunt device as claimed in claim 15 wherein the liquid solution includes a solute having a high molecular weight and wherein the solute cannot pass through the semi-permeable membrane.

17. An implantable shunt device as claimed in claim 16 wherein the solute is resistant to hydrolysis.

18. An implantable shunt device as claimed in claim 15 wherein the liquid solution is bioinert.

19. An implantable shunt device as claimed in claim 15 wherein the liquid solution in the pressurized enclosure creates an osmotic pressure between 0 and 40 mmHg.

20. An implantable shunt device as claimed in claim 15 wherein the liquid solution is a high molecular weight dextran.

21. An implantable shunt device as claimed in claim 20 wherein the dextran has a molecular weight of between 50,000 and 2,000,000 Da.

22. A method of reducing intraocular pressure comprising the steps of:

attaching a bioinert implantable shunt device to the scleral surface of an eye wherein the implantable shunt device comprises a valve apparatus having an inlet port, an outlet port, a flexible tube connected therebetween and a pressurized enclosure, the flexible tube being positioned inside the pressurized enclosure whereby fluid flow from the inlet port to the outlet port is dependent on a differential pressure between a pressure in the flexible tube and a pressure outside the flexible tube in the pressurized enclosure and the pressurized enclosure having a housing, a semi-permeable membrane in a wall of the housing and a liquid solution in the pressurized enclosure whereby fluid can pass through the semi-permeable membrane into the pressurized enclosure thereby increasing the pressure of the liquid solution in the pressurized enclosure;

inserting an inlet tube into the anterior chamber of the eye wherein the inlet tube is connected to the inlet port of the valve apparatus.

23. A method as claimed in claim 22 wherein the inlet tube is inserted through the limbus of the eye.

24. A method as claimed in claim 23 wherein the implantable shunt device is attached between the superior recutus and the lateral rectus muscles of the eye.

25. A method as claimed in claim 23 wherein the implantable shunt device is attached between the superior rectus and the medial rectus muscles.

* * * * *